(12) United States Patent
Qin et al.

(10) Patent No.: US 11,519,979 B2
(45) Date of Patent: Dec. 6, 2022

(54) SYSTEMS AND METHODS FOR AN ABDOMINAL RADIO FREQUENCY COIL FOR MR IMAGING

(71) Applicant: GE Precision Healthcare LLC, Milwaukee, WI (US)

(72) Inventors: Hilary Shuo Qin, Bellaire, TX (US); Eduardo De Leon, Milwaukee, WI (US); Fraser John Laing Robb, Aurora, OH (US); Andrea Nicole Sajewski, Mercer, PA (US); Ceara Delmore Stack, Ravenna, OH (US); Louis Jay Vannatta, Crystal Lake, IL (US); Mark Giancola, Chesterland, OH (US); Victor Taracila, Beachwood, OH (US)

(73) Assignee: GE Precision Healthcare LLC, Milwaukee, WI (US)

( * ) Notice: Subject to any disclaimer, the term of this patent is extended or adjusted under 35 U.S.C. 154(b) by 440 days.

(21) Appl. No.: 16/287,854

(22) Filed: Feb. 27, 2019

(65) Prior Publication Data
US 2020/0271738 A1 Aug. 27, 2020

(51) Int. Cl.
*A61B 5/055* (2006.01)
*G01R 33/3415* (2006.01)
*G01R 33/34* (2006.01)

(52) U.S. Cl.
CPC ........ *G01R 33/34084* (2013.01); *A61B 5/055* (2013.01); *G01R 33/34015* (2013.01); *G01R 33/3415* (2013.01)

(58) Field of Classification Search
CPC ........ G01R 33/34084; G01R 33/34015; G01R 33/3415; A61B 5/055
See application file for complete search history.

(56) References Cited

U.S. PATENT DOCUMENTS

| | | | |
|---|---|---|---|
| 6,980,002 B1 * | 12/2005 | Petropoulos | ....... G01R 33/3415 324/309 |
| 7,368,913 B2 | 5/2008 | Sellers et al. | |
| 9,116,212 B2 * | 8/2015 | Fischer | ............ G01R 33/34084 |
| 2005/0030028 A1 * | 2/2005 | Clarke | ............ G01R 33/34046 324/318 |
| 2014/0197832 A1 * | 7/2014 | Driesel | ................... H01Q 7/005 324/322 |
| 2017/0062971 A1 | 3/2017 | Boyland et al. | |
| 2017/0192067 A1 * | 7/2017 | Garcia | ............... G01R 33/3403 |

FOREIGN PATENT DOCUMENTS

WO 2018098248 A1 5/2018

* cited by examiner

*Primary Examiner* — Keith M Raymond
*Assistant Examiner* — Nicholas A Robinson

(57) ABSTRACT

Various systems and methods are provided for radio frequency coil assemblies for a magnetic resonance imaging system. In one example, a method comprises: flowing air through a plurality of airflow passages formed in a radio frequency (RF) coil assembly for a magnetic resonance imaging (MRI) system; and receiving magnetic resonance (MR) signals from an RF coil array of the RF coil assembly, wherein the RF coil array comprises a plurality of RF coil elements, each RF coil element having a loop portion which comprises two distributed capacitance wire conductors encapsulated and separated by a dielectric material.

13 Claims, 8 Drawing Sheets

SYSTEMS AND METHODS FOR AN ABDOMINAL RADIO FREQUENCY COIL FOR MR IMAGING

FIELD

Embodiments of the subject matter disclosed herein relate to magnetic resonance imaging (MRI), and more particularly, to MRI radio frequency (RF) coils.

BACKGROUND

Magnetic resonance imaging (MRI) is a medical imaging modality that can create images of the inside of a human body without using x-rays or other ionizing radiation. MRI systems include a superconducting magnet to create a strong, uniform, static magnetic field $B_0$. When a human body, or part of a human body, is placed in the magnetic field $B_0$, the nuclear spins associated with the hydrogen nuclei in tissue water become polarized, wherein the magnetic moments associated with these spins become preferentially aligned along the direction of the magnetic field $B_0$, resulting in a small net tissue magnetization along that axis. MRI systems also include gradient coils that produce smaller amplitude, spatially-varying magnetic fields with orthogonal axes to spatially encode the magnetic resonance (MR) signal by creating a signature resonance frequency at each location in the body. The hydrogen nuclei are excited by a radio frequency signal at or near the resonance frequency of the hydrogen nuclei, which add energy to the nuclear spin system. As the nuclear spins relax back to their rest energy state, they release the absorbed energy in the form of an RF signal. This RF signal (or MR signal) is detected by one or more RF coils and is transformed into the image using reconstruction algorithms.

BRIEF DESCRIPTION

In one embodiment, a method comprises: flowing air through a plurality of airflow passages formed in a radio frequency (RF) coil assembly for a magnetic resonance imaging (MRI) system; and receiving magnetic resonance (MR) signals from an RF coil array of the RF coil assembly, wherein the RF coil array comprises a plurality of RF coil elements, each RF coil element having a loop portion which comprises two distributed capacitance wire conductors encapsulated and separated by a dielectric material.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
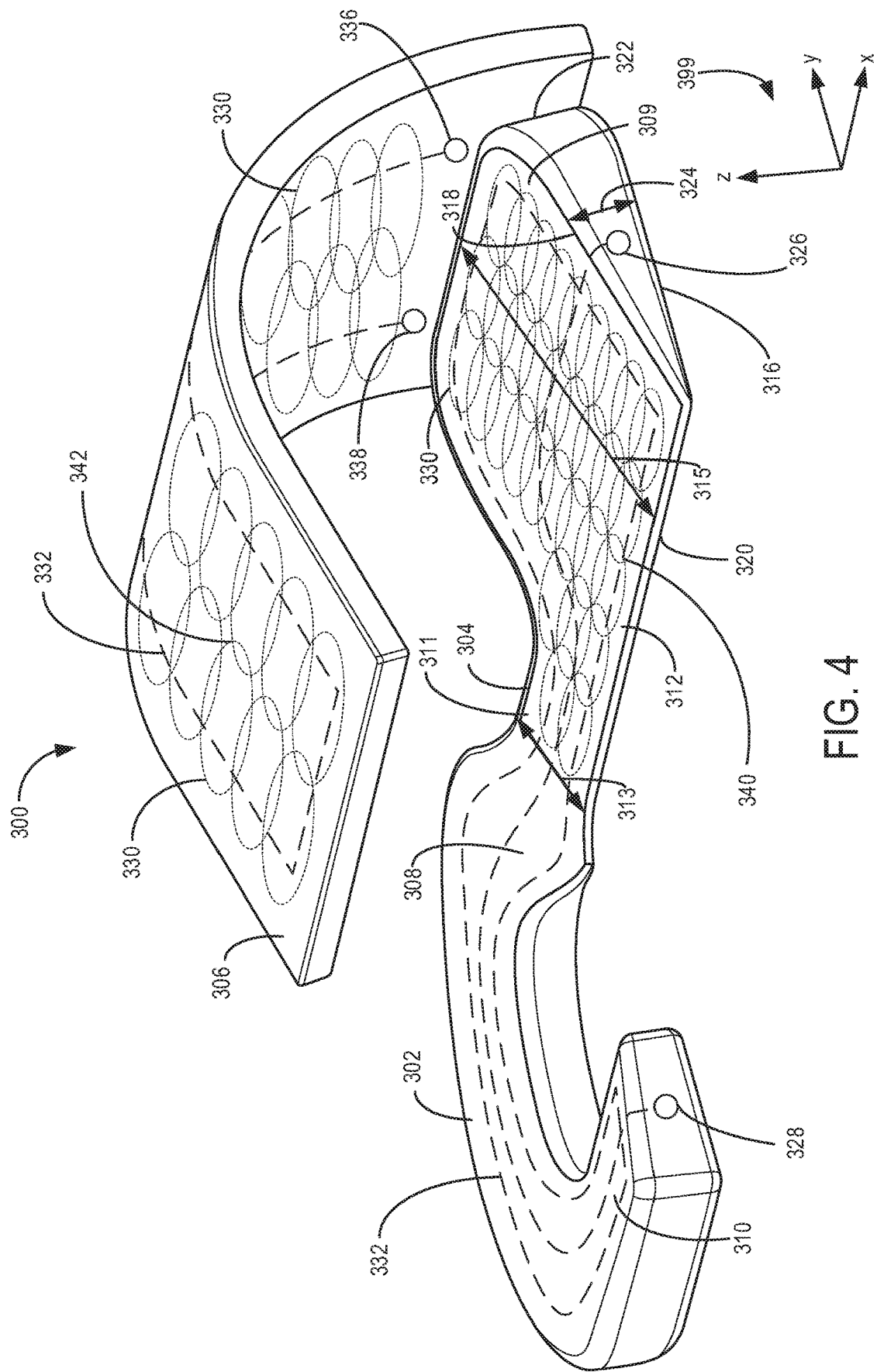
FIG. 4 shows a view of the abdominal RF coil assembly of FIG. 3 and schematically illustrates an arrangement of airflow passages and RF coil elements of the assembly.
Figure 7:
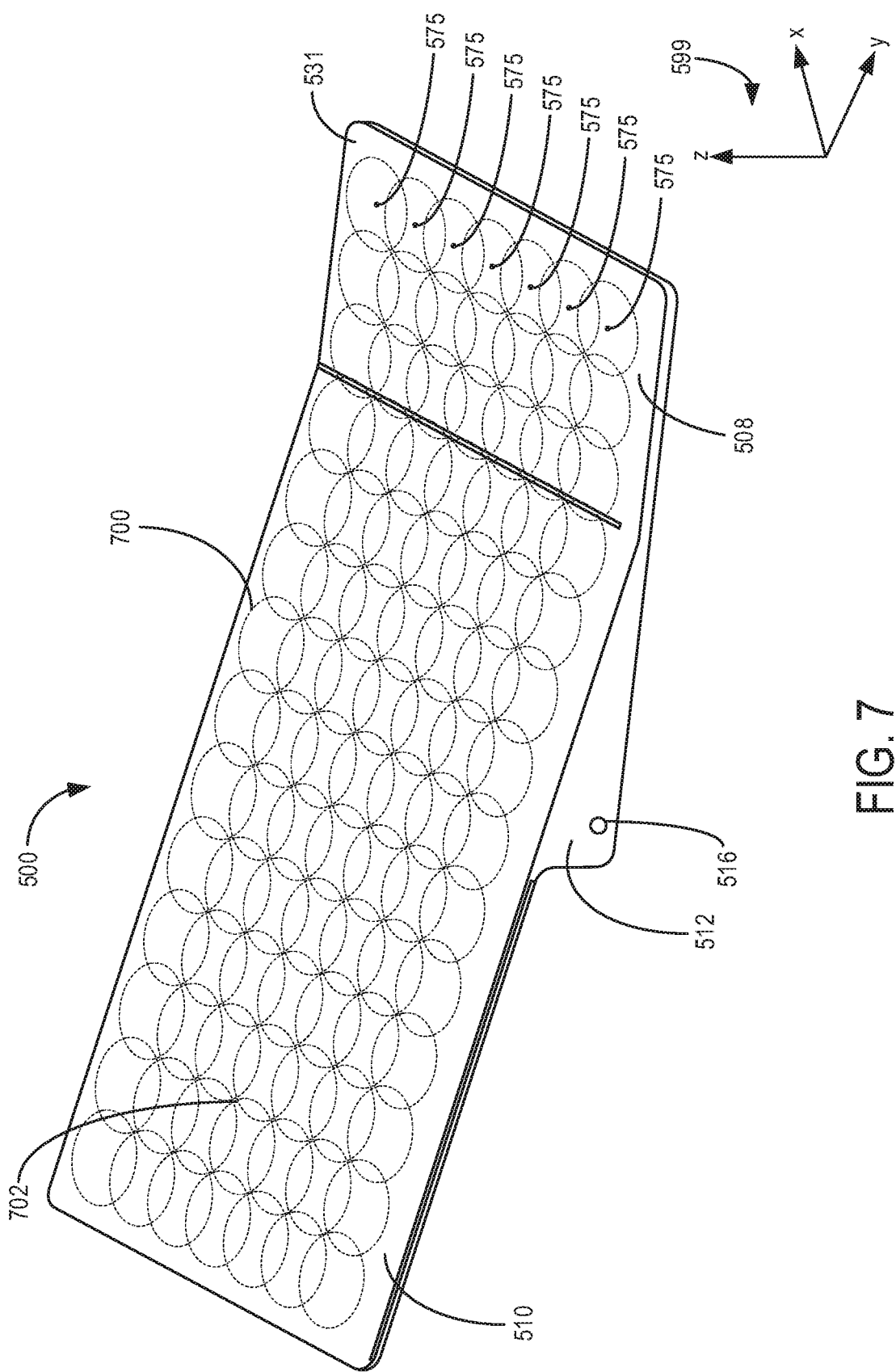
FIG. 7 shows a view of the abdominal RF coil assembly of FIGS. 5-6 with the head support removed, and illustrates an arrangement of RF coil elements of the assembly.

The following description relates to various embodiments of a radio frequency (RF) coil assembly for an MRI system. An MRI system, such as the MRI system shown by FIG. 1, includes a receive RF coil unit that may be comprised of one or more RF coil elements. For example, the receive RF coil unit may comprise an array of RF coil elements, as shown in FIGS. 4 and 7. The RF coil elements are configured with coupling electronics and distributed capacitance wire conductors, as shown in FIG. 2, such that each RF coil element is lightweight, flexible, and transparent to each other RF coil element. In this way, the RF coil assembly may be positioned against a body of a patient and wrapped around the patient in order to image portions of the body, such as the abdomen. Because the RF coil elements include the coupling electronics and distributed capacitance wire conductors, the RF coil elements may move and/or overlap relative to each other without degradation of MR signals transmitted to the MRI system.

Different patients may have different sized abdomens, as the abdominal region exhibits large variation in size across various patient populations. For example, the size of the abdominal region of different pregnant patients may vary depending on the stage of the pregnancy and the size of the individual patient. When a conventional RF coil unit is used to image the abdominal and/or torso region of a patient, this variability in the abdominal anatomy from patient to patient results in receive RF coil units that may not conform sufficiently to the patient anatomy to adequately image all areas of the anatomy. For example, the conventional RF coil unit can be difficult to position properly over the fetus due to the shape of the expecting mother's bump and motion of the fetus, which may cause the coil to slide. When the coils are strapped to the mother to prevent coil movement, they may be restrictive and the mother may experience discomfort (e.g., constriction, increased temperatures, etc.). Furthermore, in conventional fetal scanning, the mother is surrounded with pillows for support which may aggravate the overheating.

Thus, according to embodiments disclosed herein, an abdominal RF coil assembly may be configured to closely conform to the patient anatomy without causing undue discomfort to the patient. The abdominal RF coil assembly may include a plurality of RF coil elements as described above and shown in FIG. 2. Owing to the lightweight and flexible nature of the conductors and small coupling electronics of the RF coil elements, the RF coil elements may be mounted on lightweight and flexible material that may conform closely to patient anatomy and accommodate a variety of different patient sizes (e.g., for fetal scanning, spinal injury scanning, etc.).

Figure 3:
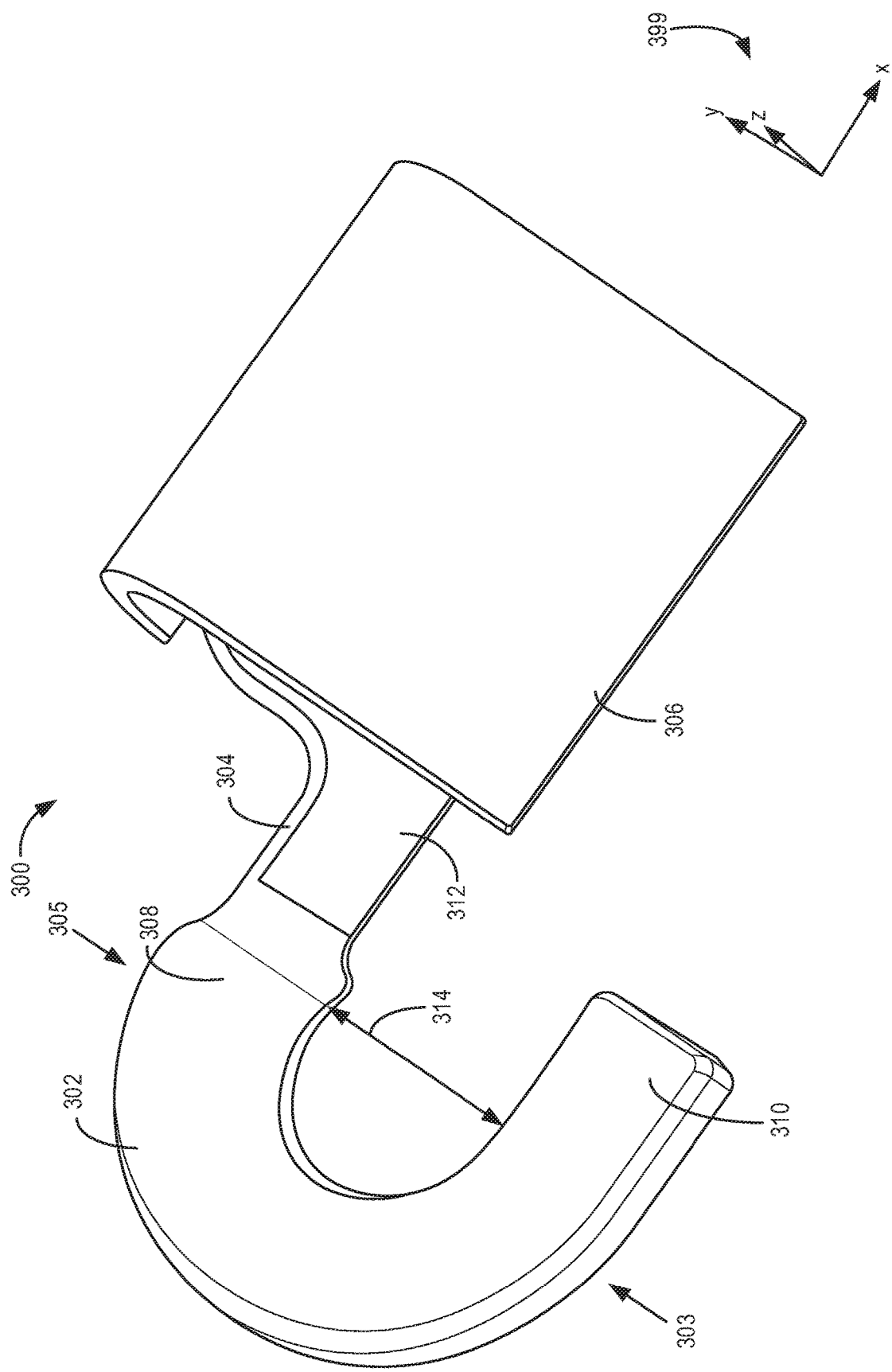
FIG. 3 shows a view of an example abdominal RF coil assembly including a head support.
Figure 8:
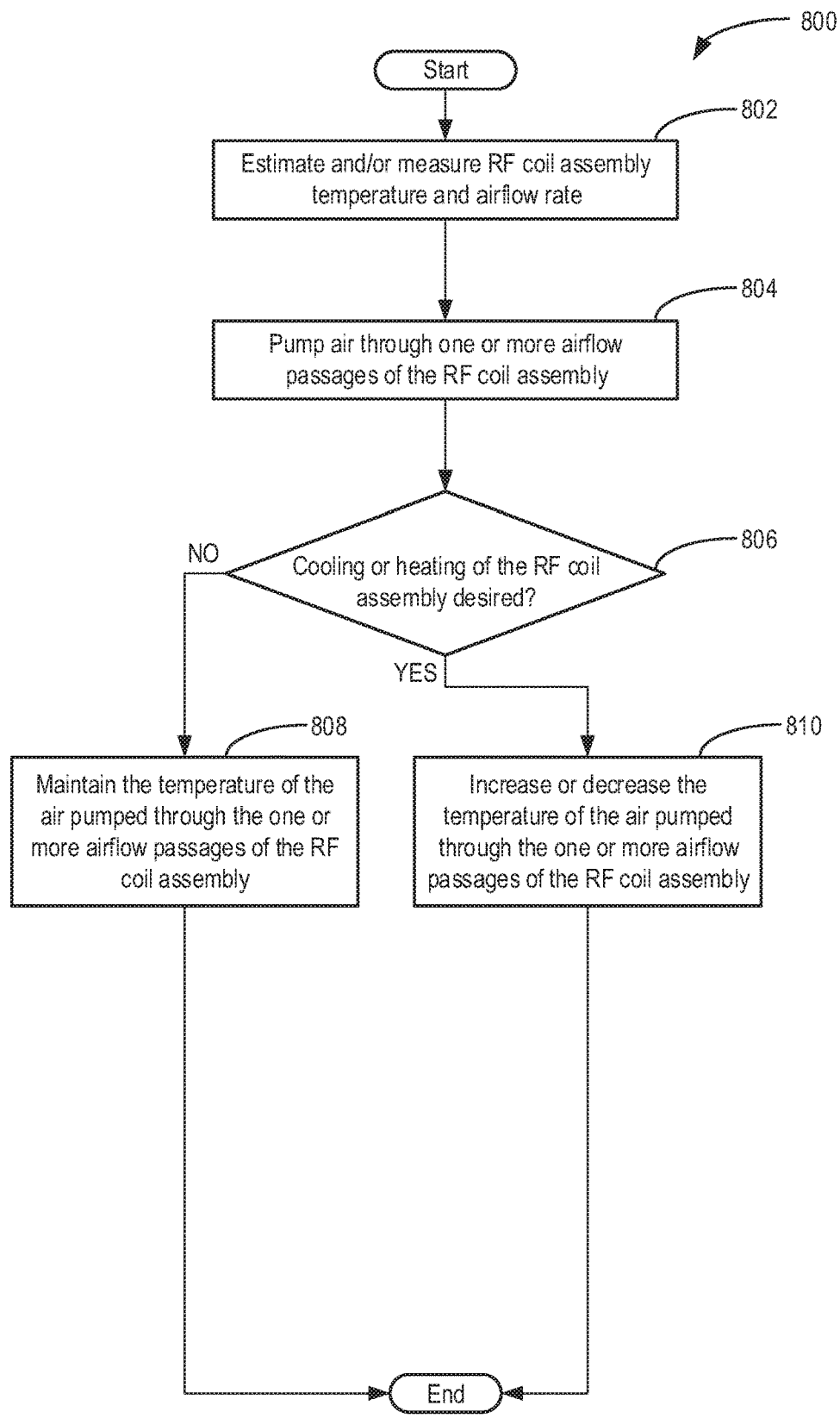
FIG. 8 shows a flowchart illustrating a method for flowing air through a plurality of airflow passages of an abdominal RF coil assembly.

For example, a first exemplary abdominal RF coil assembly, as shown in FIGS. 3-4, includes two RF coil arrays that together may be utilized to image an entire abdominal region of a patient. The first abdominal RF coil assembly includes wedge-shaped support section having a first RF coil array and a flexible foldable section having a second RF coil array. When the subject to be imaged is positioned against the wedge-shaped support section, the flexible foldable section is adapted to wrap around (e.g., cover) the abdomen of the subject such that the first RF coil array is in position to image a first side of the abdomen and the second RF coil array is in position to image the remainder of the abdomen. This arrangement may allow the RF coil elements forming the two RF coil arrays to bend and/or flex to conform around the geometry of the abdominal region. Air flow passages may be formed in the assembly in order to enable cooling (or heating) of the assembly for additional patient comfort, as illustrated by the flowchart of FIG. 8.

Figure 5:
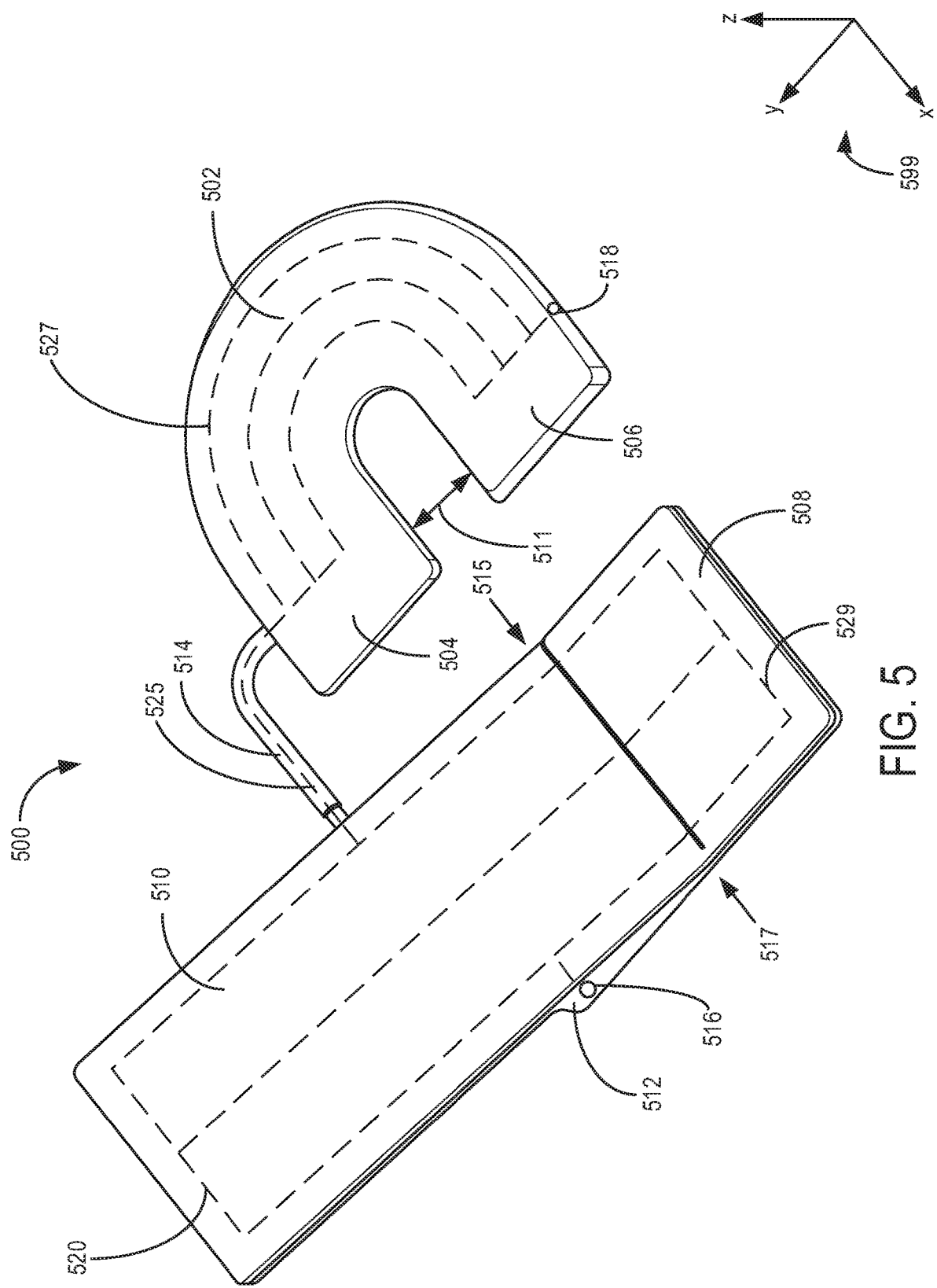
FIG. 5 shows a view of an example abdominal RF coil assembly including an adjustable head support and schematically illustrates an arrangement of airflow passages of the assembly.
Figure 6:
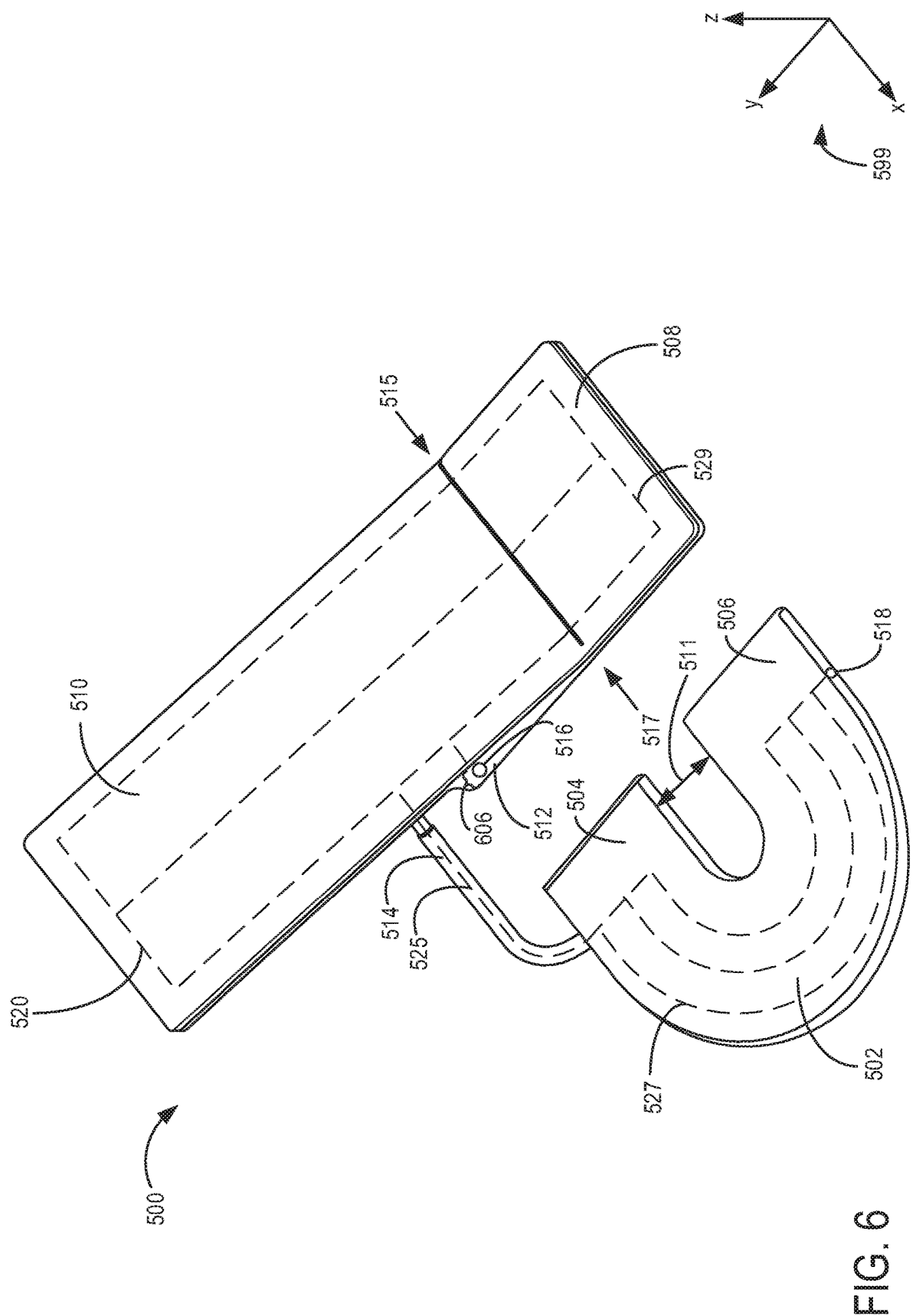
FIG. 6 shows another configuration of the abdominal RF coil assembly of FIG. 5.

A second exemplary abdominal RF coil assembly, as shown in FIGS. 5-7, includes a wedge-shaped section and a flexible, foldable section formed as one piece. A RF coil array formed by a plurality of RF coil elements are coupled to inner surfaces of the substrate of the piece. The substrate may be comprised of foam or other semi-rigid material. Various joints, hinges, or flex regions may be provided via the foam substrate rather than traditional coupling/hinging mechanisms. During imaging of a subject, a first side of the abdomen of the subject may be positioned against the wedge-shaped support section and the flexible, foldable section may be curved around the remainder of the abdomen, thereby facilitating high quality imaging of all areas of the abdominal region via the RF coil array. Air flow passages may be formed in the assembly in order to enable cooling (or heating) of the assembly for additional patient comfort. Further, the second exemplary abdominal RF coil assembly may include a head support which can be adjusted for patients of various different sizes and for different body positions.

Figure 1:
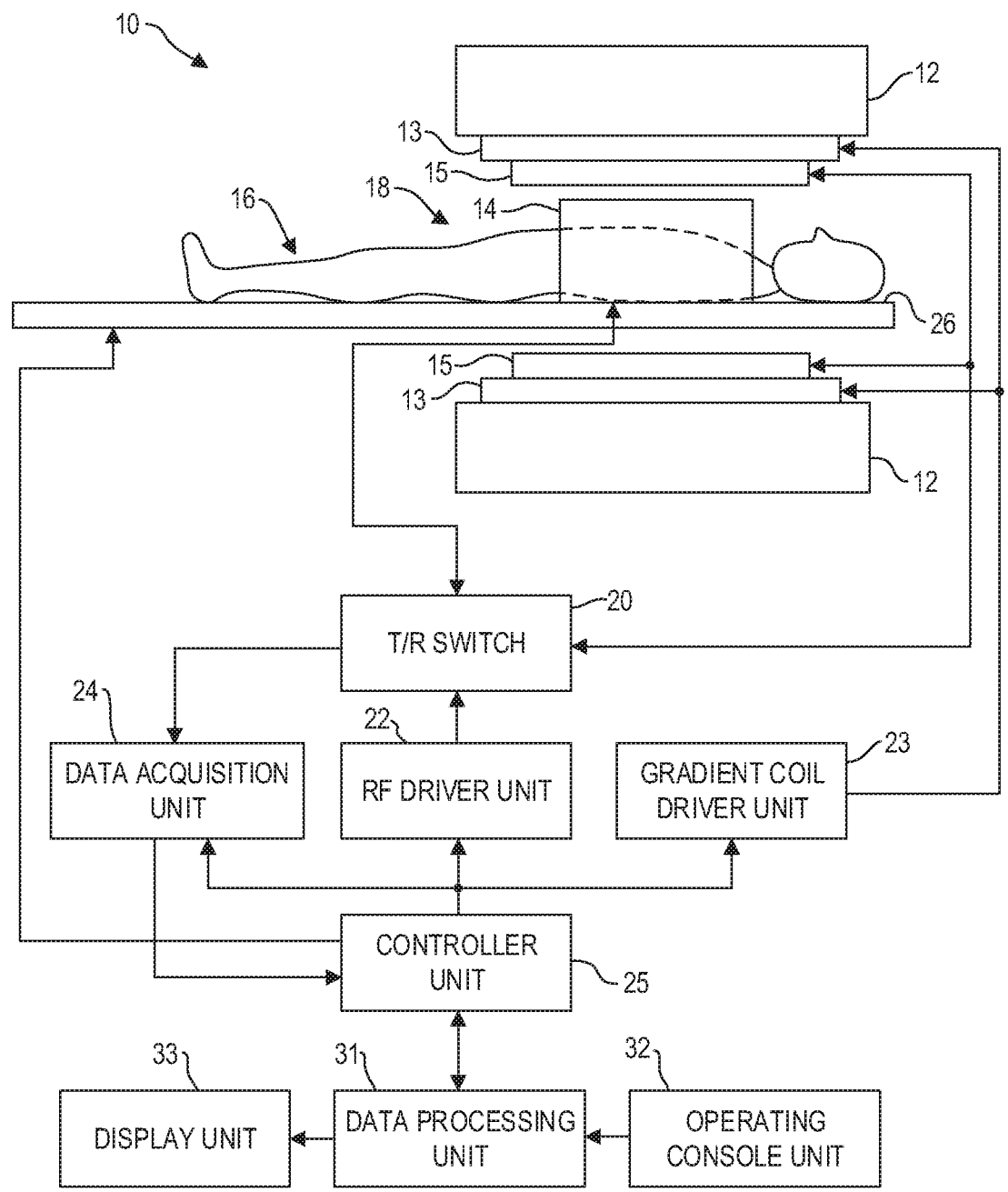
FIG. 1 is a block diagram of an MRI system according to an exemplary embodiment.
Figure 2:
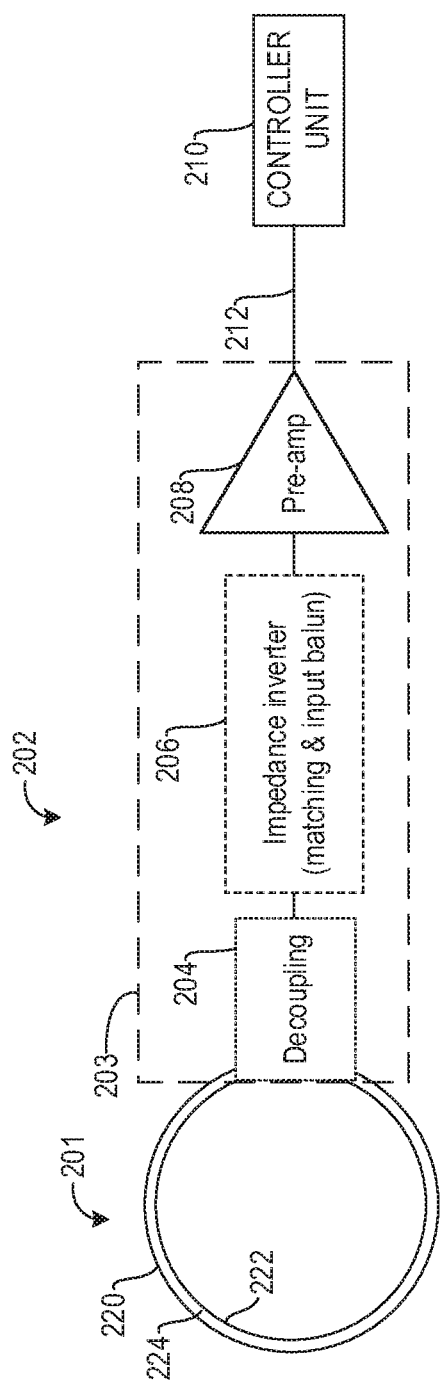
FIG. 2 schematically shows an example RF coil element coupled to a controller unit, in accordance with an exemplary embodiment.

FIG. 1 illustrates a magnetic resonance imaging (MRI) apparatus 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

During a scan, RF coil array interfacing cables (not shown in FIG. 1) may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local surface RF coil unit 14 receives the MR signals. More generally, RF coils are used to transmit RF excitation signals ("transmit coil"), and to receive the MR signals emitted by an imaging subject ("receive coil"). In some embodiments, the transmit and receive coils are a single mechanical and electrical structure or array of structures, with transmit/receive mode switchable by auxiliary circuitry. In other examples, the transmit body coil (e.g., RF body coil unit 15) and the surface receive coil (e.g., RF coil unit 14) may be separate components. For enhanced image quality, however, it may be desirable to provide a receive coil that is mechanically and electrically isolated from the transmit coil. In such case it is desirable that the receive coil, in its receive mode, be electromagnetically coupled to and resonant with an RF "echo" that is stimulated by the transmit coil. However, during transmit mode, it may be desirable that the receive coil is electromagnetically decoupled from and therefore not resonant with the transmit coil, during actual transmission of the RF signal. Such decoupling averts a potential problem of noise produced within the auxiliary circuitry when the receive coil couples to the full power of the RF signal. Additional details regarding the uncoupling of the receive RF coil will be described below.

Turning now to FIG. 2, a schematic view of an RF coil element 202 coupled to a controller unit 210 is shown according to an exemplary embodiment. The RF coil element 202 includes a loop portion 201 and a coupling electronics portion 203 which is coupled to the controller unit 210 via a coil-interfacing cable 212. In some embodiments, the RF coil element may be used in a surface receive coil, which may be single- or multi-channel. The RF coil element 202 may be used in RF coil unit 14 of FIG. 1 and as such may operate at one or more frequencies in the MRI apparatus 10. The coil-interfacing cable 212 may extend between the electronics portion 203 and an interfacing connector of an RF coil array and/or between the interfacing connector of the RF coil array and the MRI system controller unit 210. The controller unit 210 may correspond to and/or be associated with the data processing unit 31 and/or controller unit 25 in FIG. 1.

The loop portion 201 may be comprised of at least two parallel conductors that form a distributed capacitance along the length of the loop portion. In the example shown in FIG. 2, the loop portion 201 includes a first conductor 220 and a second conductor 222 which exhibit a substantially uniform capacitance along the entire length of the loop portion. Distributed capacitance (DCAP), as used herein, represents a capacitance exhibited between conductors that distributes along the length of the conductors and may be void of discrete or lumped capacitive components and discrete or lumped inductive components. The DCAP can also be called incorporated capacitance. In some embodiments, the capacitance may distribute in a uniform manner along the length of the conductors.

A dielectric material 224 encapsulates and separates the first and second conductors 220, 222. The dielectric material 224 may be selected to achieve a desired distributive capacitance. For example, the dielectric material 224 may be selected based on a desired permittivity $\varepsilon$. In particular, the dielectric material 224 may be air, rubber, plastic, or any other appropriate dielectric material. In some embodiments, the dielectric material may be polytetrafluoroethylene (pTFE). The dielectric material 224 may surround the parallel conductive elements of the first and second conductors 220, 222. Alternatively, the first and second conductors 220, 222 may be twisted upon one another to from a twisted pair cable. As another example, the dielectric material 224 may be a plastic material. The first and second conductors 220, 222 may form a coaxial structure in which the plastic dielectric material 224 separates the first and second conductors. As another example, the first and second conductors may be configured as planar strips.

The coupling electronics portion 203 is connected to the loop portion 201 of the RF coil element 202. Herein, the coupling electronics portion 203 may include a decoupling circuit 204, impedance inverter circuit 206, and a pre-amplifier 208. The decoupling circuit 204 may effectively decouple the RF coil during a transmit operation. Typically, the RF coil element 202 in its receive mode may receive MR signals from a body of a subject being imaged by the MR apparatus. If the RF coil element 202 is not used for transmission, then it may be decoupled from the RF body coil while the RF body coil is transmitting the RF signal.

The impedance inverter circuit 206 may include an impedance matching network between the loop portion 201 and the pre-amplifier 208. The impedance inverter circuit 206 is configured to transform an impedance of the loop portion 201 into an optimal source impedance for the pre-amplifier 208. The impedance inverter circuit 206 may include an impedance matching network and an input balun. The pre-amplifier 208 receives MR signals from the loop portion 201 and amplifies the received MR signals. In one example, the pre-amplifier 208 may have a low input impedance configured to accommodate a relatively high blocking or source impedance. The coupling electronics portion 203 may be packaged in a very small PCB, e.g., approximately 2 cm$^2$ in size or smaller. The PCB may be protected with a conformal coating or an encapsulating resin.

The coil-interfacing cable 212, such as a RF coil array interfacing cable, may be used to transmit signals between the RF coils and other aspects of the processing system. The RF coil array interfacing cable may be disposed within the bore or imaging space of the MRI apparatus (such as MRI apparatus 10 of FIG. 1) and subjected to electro-magnetic fields produced and used by the MRI apparatus. In MRI systems, coil-interfacing cables, such as coil-interfacing cable 212, may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents. Thus, coil-interfacing cable 212 may include one or more baluns. In some embodiments, the one or more baluns may be continuous baluns, such as distributed, flutter, and/or butterfly baluns. The cable 212 may be a 3-conductor triaxial cable having a center conductor, an inner shield, and an outer shield. In some embodiments, the center conductor is connected to the RF signal and pre-amp control (RF), the inner shield is connected to ground (GND), and the outer shield is connected to the multi-control bias (diode decoupling control) (MC_BIAS).

Structure of the loop portion and the coupling electronics portion is described in more detail in PCT Application No. US2017/062971 (published as WO2018/098248), which is incorporated herein by reference.

The RF coil element presented above with respect to FIG. 2 may be utilized in order to receive MR signals during an MR imaging session. As such, the RF coil element of FIG. 2 may be used in RF coil unit 14 of FIG. 1 and may be coupled to a downstream component of the MRI system, such as the controller unit 25. The RF coil unit may be placed in the bore of the MRI system in order to receive the MR signals during the imaging session, and thus may be in proximity to the transmit RF coil (e.g., the body RF coil unit 15 of FIG. 1). The controller unit may store instructions in non-transitory memory that are executable to generate an image from an imaging subject positioned in the bore of the MRI system during an MR imaging session. To generate the image, the controller unit may store instructions to perform a transmit phase of the MR imaging session. During the transmit phase, the controller unit may command (e.g., send signals) to activate the transmit RF coil(s) in order to transmit one or more RF pulses. To prevent interference leading to $B_1$ field distortion during the transmit phase, the receive RF coil(s) may be decoupled during the transmit phase. The controller unit may store instructions executable to perform a subsequent receive phase of the MR imaging session. During the receive phase, the controller unit may obtain MR signals from the receive RF coil(s). The MR signals are usable to reconstruct the image of the imaging subject positioned in the bore of the MRI system.

FIG. 3 shows a top perspective view of an abdominal RF coil assembly 300, in accordance with an exemplary embodiment. The abdominal RF coil assembly 300 includes a first section 302 adapted to support a head of a subject (e.g., a patient) to be imaged by an MRI system, a second section 304 adapted to support an abdominal region of the subject, and a third section 306 (which may be referred to herein as a foldable section) adapted to curve around the remainder of the abdominal region of the subject (e.g., the portion of the abdominal region not already supported/in contact with second section 304). The first section 302 and second section 304 may be referred to herein collectively as a support section. The second section 304 includes a first RF coil array 340 and the third section 306 includes a second RF coil array 342, as shown by FIG. 4 and described further below. Each of the first RF coil array 340 and second RF coil array 342 includes a plurality of RF coil elements 330 similar to the RF coil element 202 described above with respect to FIG. 2. Reference axes 399 are provided in FIGS. 3-4 for comparison of the views shown.

In the example shown by FIGS. 3-4, the first section 302 is joined to the second section 304 of the abdominal RF coil assembly 300 as a single, continuous unit (e.g., the first section 302 and second section 304 may be formed together as a single, unitary piece). However, in other examples, the first section 302 may instead be removably coupled with the second section 304 (e.g., separable from the second section 304). As described above, the first section 302 is adapted to support the head of the subject to be imaged by an MRI system (e.g., the MRI apparatus 10 described above with reference to FIG. 1) via the abdominal RF coil assembly 300. Specifically, the first section 302 includes a first extension 308, a second extension 310, and an opening 314 is formed between the first extension 308 and second extension 310. The first extension 308 and second extension 310 are joined together (e.g., molded together) and curve around the opening 314 such that the first section 302 forms a U-shape having a first side 303 and an opposing, second side 305. During conditions in which the head of the subject is supported by the first section 302, a front of the head (e.g., the face) may be positioned at the second side 305, and a rear of the head may be positioned at the first side 303 (e.g., the subject may be positioned on his or her side). In this configuration, the front of the head is supported by the first extension 308, the rear of the head is supported by the second extension 310, and an ear of the patient may be positioned within opening 314 to increase patient comfort.

In addition to the support for the head of the subject provided by the first section 302 as described above, the second section 304 of the abdominal RF coil assembly 300 is adapted to provide support for the abdominal region of the subject. As illustrated by FIG. 4, the second section 304 includes a wedge base 309 increasing in thickness 324 from inner edge 320 of the second section 304 (e.g., the edge positioned toward the first extension 308 of the first section 302) to outer edge 322 of the second section 304 (e.g., the edge positioned opposite to the inner edge 320, away from the first extension 308 of the first section 302). Specifically, the thickness 324 of the second section 304 between top surface 318 of the second section 304 and bottom surface 316 of the second section 304 increases in the direction from inner edge 320 to outer edge 322. The wedge base 309 is joined with an extension portion 311 coupled to the first section 302, with the extension portion 311 having a reduced size relative to the wedge base 309. For example, a width 313 of the extension portion 311 may be approximately the same as a width of the first extension 308 of the first section 302 (with the width 313 being smaller than a width 315 of the wedge base 309 in the same direction). During conditions in which the abdominal RF coil assembly 300 is utilized for imaging the subject, the head of the subject may be positioned against the first section 302 as described above (e.g., with the front of the head facing toward the first extension 308) and the abdomen of the subject may be positioned against the wedge base 309 of the second section 304. By configuring the thickness of the wedge base 309 of the second section 304 to increase toward the outer edge 322 as described above, the second section 304 may elevate the abdomen of the subject relative to a rear of the subject during conditions in which the abdomen of the subject is positioned against the second section 304. Elevating the abdomen may improve the imaging quality of the abdomen via the RF coil array 340 and/or RF coil array 342, each described below.

As described above, the second section 304 includes the first RF coil array 340 and the third section 306 includes the second RF coil array 342. Each of the RF coil elements 330 of the first RF coil array 340 and second RF coil array 342 may be a non-limiting example of the RF coil element 202 illustrated in FIG. 2 and described above, which includes a loop portion (e.g., comprised of at least two parallel, distributed capacitance wire conductors encapsulated and separated by a dielectric material) and a coupling electronics portion. The coupling electronics portion may include a pre-amplifier, a decoupling circuit, and an impedance inverter circuit, as described above. In the example shown by FIG. 4, the first RF coil array includes 32 RF coils in order to image the portion of the abdomen of the subject positioned against the second section 304. However, in other configurations, the first RF coil array may include a different number of RF coils (e.g., 16 RF coils). The second RF coil array 342 may include a suitable number of RF coils for imaging the remainder of the abdomen of the subject (e.g., 32 RF coils, 48 RF coils, etc.). In some examples, each loop portion of each RF coil may have the same diameter. In an example, each diameter may be 6 cm. Each RF coil may overlap with neighboring RF coils of the plurality of RF coils by an equal amount. In other examples, one or more of the RF coils may overlap with neighboring RF coils by a different amount.

Each RF coil element of the first RF coil array 340 may be coupled to the second section 304 in a suitable manner, such as stitching. In one example, each RF coil element of the first RF coil array 340 may be embedded within a material of the second section 304. For example, the second section 304 may be molded to include the first RF coil array 340 positioned internally within the material of the second section 304. As another example, the second section 304 may comprise one or more layers of material, and the first RF coil array 340 may be positioned between two or more of the layers. Similarly, each RF coil of the second RF coil array 340 may be coupled to the third section 306 in a suitable manner (e.g., stitched to the third section 306, embedded within a material of the third section 306, etc.).

In some examples, the second section 304 and third section 306 may be formed from a same material suitable for MRI imaging. For example, the material may be transparent to RF signals and may maintain a desired rigidity while allowing some flexibility and conformability, such as polyurethane foam, polystyrene, nylon, or other suitable material. In some examples, the different regions described herein may be comprised of different pieces of material that are coupled together. When separate pieces of material are coupled together, they pieces may be coupled together using adhesive, thermal welding, or other non-rigid coupling mechanism, thereby avoiding the use of rigid joints, hinges, or other mechanisms. In other examples, two or more of the regions described herein may be comprised of a single piece of material. For example, the first section 302, second section 304, and/or third section 306 may be made from one piece of material that is cut/shaped to form the assembly shown.

The internal electronics (e.g., coupling electronics portions, baluns, coil-interfacing cable) may be embedded within the material (e.g., embedded within the foam) and the loop portions may be coupled on surfaces of the material. In some examples, one or more of the sections may be covered in an outer cover to protect the internal components and maintain sterility, where the cover is thin and flexible (e.g., formed of a flexible material that is transparent to RF signals, such as one or more layers of Nomex® material or Nomex Nano® material). In still other examples, one or more of the sections may be comprised of an outer substrate that is shaped as shown herein once filled with a filler material, where the filler material is comprised of discrete particles.

In some examples, the third section 306 may be configured from a different material than the second section 304 in order to increase a flexibility of the third section 306 relative to the second section 304. For example, the second section 304 may be formed of a material (e.g., foam) configured to have sufficient strength (e.g., rigidity) to support a weight of the abdomen of the subject to be imaged while additionally having enough elasticity to increase patient comfort. However, the third section 306 may be formed of a different material having a greater flexibility than the material of the second section 304 such that the third section 306 may wrap around (e.g., cover) the abdomen of the subject and conform to the shape of the abdomen. By increasing the flexibility of the third section 306 relative to the second section 304, the RF coils of the second RF coil array 342 may be positioned closer to the anatomy to be imaged (e.g., the abdomen). Further, by elevating the abdomen of the subject via the second section 304 as described above, the abdomen may be positioned at a more suitable angle to facilitate the third section 306 to wrap around the remainder of the abdomen, and imaging quality may be increased.

A coil-interfacing cable may extend between each coupling electronics portion of the RF coil elements of the first RF coil array 340 and an RF coil interfacing connector. Similarly, a coil-interfacing cable may extend between each coupling electronics portion of the RF coil elements of the second RF coil array 342 and an RF coil interfacing connector. For each RF coil array, each of the electrical wires coupled to the corresponding coupling electronics portions may be housed together (e.g., bundled together) within the corresponding coil-interfacing cable and electrically coupled to the corresponding connector. The connector may interface with the MRI system (e.g., electrically couple with the MRI system by plugging into an input of the MRI system) in order to output signals from the RF coils to the MRI system, and the MRI system may process the signals received from the RF coils via the connector in order to produce images of the body of the patient (e.g., images of the anatomical features of the patient to be imaged by the abdominal RF coil assembly 300). In some examples, a single coil-interfacing cable may be coupled to both of the first RF coil array 340 and second RF coil array 342, and the MRI system may process the signals received from the RF coils of both of the first RF coil array 340 and second RF coil array 342 via a single connector.

Each RF coil element of the first RF coil array 340 and each RF coil element of the second RF coil array 342 may be configured similarly (e.g., including a loop portion and a coupling electronics portion). In some examples, the loop portion of each RF coil element of the first RF coil array 340 may have the same diameter and/or the loop portion of each RF coil element of the second RF coil array 342 may have the same diameter. In an example, the diameter of the RF coil elements of the first RF coil array 340 may be a first, smaller diameter (e.g., 8 cm) and the diameter of the RF coil elements of the second RF coil array 342 may be a second, larger diameter (e.g., 10 cm). In yet another example, the diameter of the RF coil elements of the first RF coil array 340 may be the same as the diameter of the RF coil elements of the second RF coil array 342.

In the example shown by FIG. 4, the abdominal RF coil assembly 300 includes a plurality of airflow passages 332 configured to enable the various sections of the abdominal RF coil assembly 300 to be heated and/or cooled as desired to increase patient comfort. An example arrangement of the airflow passages 332 is shown by FIG. 4, with the position of the airflow passages 332 indicated by long dashed lines. Although the airflow passages 332 are illustrated at the outer surfaces of the abdominal RF coil assembly 300 in FIG. 4, it should be appreciated that the airflow passages 332 are formed internally within the material of each of the corresponding sections. For example, the airflow passages 332 may be comprised of voids (e.g., channels) formed within the material of the first section 302, second section 304, and third section 306 during manufacture of the abdominal RF coil assembly 300. In another example, the airflow passages 332 of one or more of the sections (e.g., the third section 306) may comprise tubes or other separate, hollow components embedded within the material of the corresponding section during manufacture of the abdominal RF coil assembly 300. For example, the airflow passages 332 of the first section 302 and second section 304 may be voids formed within the material of the first section 302 and second section 304, while the airflow passages 332 of the third section 306 may be flexible conduits embedded within the material of the third section 306.

The airflow passages 332 of the first section 302 and second section 304 may be joined together such that air (or other fluids) may flow from the second section 304 to the first section 302 (or vice versa). For example, air may be pumped into port 326 positioned at an exterior end of the second section 304, and the air may flow through the airflow passages 332 into the first section 302 and out of port 328 positioned at an exterior end of the first section 302. The third section 306 is shown in FIG. 4 to include port 336 and port 338 positioned at an exterior of the third section 306. In one example, air may be pumped into port 336 to flow through the airflow passages 332 of the third section 306, and may flow out of port 338. In another example, the airflow passages 332 of the first section 302 and second section 304 may additionally be fluidly coupled with the airflow passages of the third section 306, such that air may be pumped through each of the first section 302, second section 304, and third section 306 via a single port.

In order to adjust the temperature of the various sections of the abdominal RF coil assembly 300, an operator of the abdominal RF coil assembly 300 (e.g., an MRI technician) may vary the temperature of the air flowing into the airflow passages 332. For example, during operation of the abdominal RF coil assembly 300, the temperature of the RF coils may be increased. In order to reduce a temperature of the abdominal RF coil assembly 300, the operator may decrease the temperature of the air flowing into the airflow passages 332 and/or increase a flow rate of air into the airflow passages 332. In this way, the temperature of the abdominal RF coil assembly 300 may be regulated for increased patient comfort. In other examples, one or more of the airflow passages may be coupled to a temperature sensor, and output from the temperature sensor may be utilized by a controller or other computing device to automatically maintain the temperature of the air flowing in the airflow passages at or below a threshold temperature (e.g., by adjusting a level of cooling of the air provided by a heat exchanger positioned upstream of the airflow passages, for example). In some examples, the level of cooling provided by the air flowing in the airflow passages may be adjusted by adjusting a flow rate of the air flowing in the airflow passages. In still further examples, the temperature and/or flow rate of the air flowing through the airflow passages may be relatively unregulated (e.g., the air may be room temperature air that is flowed at a fixed flow rate).

In some examples, one or more surfaces of one or more of the first section 302, second section 304, and third section 306 configured to be in contact with surfaces of the body of the subject to be imaged may include orifices (e.g., holes) fluidly coupled with the airflow passages 332. Air may flow through the airflow passages 332 and a portion of the air may flow out of the orifices in order to provide direct cooling and/or heating to the body of the subject. For example, the head of the subject may be supported by the first section 302 and the abdominal portion of the subject may be supported by the second section 304, and air may flow out of the airflow passages 332 and directly contact the surfaces of the body of the subject positioned against the first section 302 and second section 304 in order to directly cool and/or heat the body of the subject. As a result, patient comfort may be increased.

FIGS. 5-7 each show different views and configurations of an abdominal RF coil assembly 500, in accordance with another exemplary embodiment. Reference axes 599 are provided in each of FIGS. 5-7 for comparison of the views shown. Abdominal RF coil assembly 500 includes a first section 502, a second section 508, and a third section 510 (which may be referred to herein as a foldable section). The first section 502 and second section 508 may be referred to collectively herein as a support section. First section 502 includes a first extension 504 and a second extension 506 separated by an opening 511 such that the first section 502 has a U-shape, similar to the first section 302 described above with reference to FIGS. 3-4. During conditions in which the abdominal RF coil assembly 500 is utilized to image a subject (e.g., image a patient via an MRI system, such as the MRI apparatus 10 described above with reference to FIG. 1), the head of the subject may be supported by the first section 502, similar to the support provided by the first section 302 as described above.

The first section 502 is coupled to a wedge base 512 of the second section 508 via an adjustable arm 514. The adjustable arm 514 is configured such that an operator of the abdominal RF coil assembly 500 may adjust the adjustable arm 514 (e.g., shorten or lengthen the adjustable arm 514) in order to adjust the position of the first section 502 relative to the second section 508. For example, the adjustable arm 514 may include one or more telescoping elements (e.g., nested tubes) to enable the length of the adjustable arm 514 to increase or decrease as desired by the operator. In this way, the position of the first section 502 may be adjusted in order to provide head support for patients of various different sizes. In some examples, the adjustable arm 514 (which may be referred to herein as a telescoping arm) may be pivotably coupled to wedge base 512 such that the adjustable arm 514 may pivot at the wedge base 512 in order to position the first section 502 at an opposing side of the abdominal RF coil assembly 500. As one example, in the position illustrated by FIG. 5, the first section 502 is positioned at a first side 515 of the second section 508 and third section 510. In an alternate configuration illustrated by FIG. 6, the adjustable arm 514 may be rotated such that the first section 502 is positioned at an opposing, second side 517 of the second section 508 and third section 510. The adjustable arm 514 is configured to rotate the first section 502 relative to the second section 508 in accordance with different body positions of the subject. In this way, the head of the patient/imaging subject may be supported by the first section 502 when the patient is lying on a first side (e.g., lying on the left side) or a second side (e.g., lying on the right side) of the patient's body.

As described above, the second section 508 of the abdominal RF coil assembly 500 includes wedge base 512. A thickness 606 of the wedge base 512 (shown by FIG. 6) increases as the wedge base 512 extends toward the adjustable arm 514. In this configuration, during conditions in which a head of a subject to be imaged is supported by the first section 502 and an abdominal portion of the subject is supported by the second section 508, the increasing thickness of the wedge base 512 results in elevation of the abdominal portion for increased ease of imaging and patient comfort.

The third section 510 is coupled to the second section 508 and extends in a direction away from the wedge base 512 and adjustable arm 514. In some examples, the third section 510 may be formed from a same material as the second section 508 (e.g., foam, one or more layers of Nomex® material, etc.). In another example, the third section 510 may be formed from a different material than the second section 508. The third section 510 is configured to have a greater amount of flexibility relative to the second section 508 such that the third section 510 may be wrapped around the abdominal portion of the subject to be imaged during conditions in which the subject is supported by the abdominal RF coil assembly 500.

As illustrated by FIG. 5, the first section 502, second section 508 and third section 510 each include a plurality of airflow passages (indicated by long dashed lines). Similar to the airflow passages 332 described above with reference to the abdominal RF coil assembly 300 shown by FIGS. 3-4, airflow passages 527 of the first section 502, airflow passages 529 of the second section 508, and airflow passages 520 of the third section 510 are illustrated at the outer surfaces of the abdominal RF coil assembly 500 in FIG. 5. However, it should be appreciated that the airflow passages 520, 527, and 529 are formed internally within the material of each of the corresponding sections. For example, the airflow passages 527 may comprise voids (e.g., channels) formed within the material of the first section 502, airflow passages 529 may comprise voids formed within the material of the second section 508, and airflow passages 520 may comprise voids formed within the material of the third section 510 during manufacture of the abdominal RF coil assembly 500. In another example, the airflow passages of one or more of the sections (e.g., the airflow passages 520 of third section 510) may comprise tubes or other separate, hollow components embedded within the material of the corresponding section during manufacture of the abdominal RF coil assembly 500. For example, the airflow passages 527 of the first section 502 and airflow passages 529 of the second section 508 may be voids formed within the material of the first section 502 and second section 508 respectively, while the airflow passages 520 of the third section 510 may be flexible conduits embedded within the material of the third section 510. The airflow passages 529 of the second section 508 may be fluidly coupled with the airflow passages 520 of the third section 510 within an interior of the second section 508 and third section 510.

The airflow passages described above may be positioned within the interior of the corresponding sections of the abdominal RF coil assembly 500 such that the airflow passages do not intersect with the RF coils. For example, with regard to the second section 508, the RF coils disposed within the second section 508 may be positioned closer to an outer surface 531 of the second section 508 (shown by FIG. 7) adapted to be in face-sharing contact with the body of the subject to be imaged, while the airflow passages 529 of the second section 508 may be positioned further from the outer surface 531 than the RF coils within the interior of the second section 508. In this configuration, the RF coils may be positioned closer than the RF coils to the body of the subject in order to improve imaging quality.

In some examples, one or more surfaces of one or more of the first section 502, second section 508, and third section 510 configured to be in contact with surfaces of the body of the subject to be imaged (e.g., the outer surface 531 of second section 508) may include orifices (e.g., holes) fluidly coupled with the corresponding airflow passages of the one or more corresponding sections. For example, the first section 502 may include orifices fluidly coupled with the airflow passages 527 of the first section 502, the second section 508 may include orifices fluidly coupled with the airflow passages 529 of the second section 508, and/or the third section 510 may include orifices fluidly coupled with the airflow passages 520 of the third section 510. Air may flow through the airflow passages and a portion of the air may flow out of the orifices in order to provide direct cooling and/or heating to the body of the subject. For example, the head of the subject may be supported by the first section 502 and the abdominal portion of the subject may be supported by the second section 508, and air may flow out of the airflow passages 527 of the first section 502 and airflow passages 529 of the second section 508 and directly contact the surfaces of the body of the subject positioned against the first section 502 and second section 508 in order to directly cool and/or heat the body of the subject. As a result, patient comfort may be increased.

In some examples, the orifices may be positioned such that the orifices do not overlap the RF coils and associated coupling electronics disposed within the corresponding sections. For example, for each orifice, the orifice may be positioned approximately at a center of a loop portion of a corresponding RF coil element of RF coil array 702 and may not overlap any portion of the corresponding RF coil element (e.g., coupling electronics portion). An example positioning of the orifices is illustrated by orifices 575 shown by FIG. 7. Each of the orifices 575 may be fluidly coupled to one or more of the airflow passages 529 of the second section 508 as described above. In this configuration, because the orifices do not overlap the RF coils, flowing air from the airflow passages to the plurality of orifices includes flowing air out of the orifices only at locations that do not overlap the plurality of RF coils (e.g., locations in which portions of the RF coils are not positioned directly below the orifices within the thickness of the interior of the sections of the abdominal RF coil assembly).

The adjustable arm 514 may additionally include one or more airflow passages 525 fluidly coupling the airflow passages 527 of the first section 502 with the airflow passages 529 of the second section 508 and airflow passages 520 of the third section 510. As one example, air may flow through the first section 502 (e.g., air may be pumped into a port 518 positioned at an exterior of the first section via an air pump) and into the one or more airflow passages 525 of the adjustable arm 514, where the one or more airflow passages 525 within the adjustable arm 514 may direct the air from the first section 502 to the airflow passages 529 of the second section 508 and airflow passages 520 of the third section 510. The air may then flow out of the second section 508 and/or third section 510 via a second port 516 positioned at an exterior of the second section 508 or third section 510 (e.g., positioned at the wedge base 512 in FIG. 5). In this configuration, the airflow passages 520 enable air (or other fluid) to flow through the abdominal RF coil assembly 500 via a single input (e.g., input port) and a single output (e.g., output port), which may reduce an amount of additional equipment (e.g., air pumps) utilized to flow air through the abdominal RF coil assembly 500.

In some examples, one or more of the ports of the abdominal RF coil assembly 500 may be positioned differently relative to the positions illustrated by FIG. 5. For example, the first section 502 may include port 518 positioned at an underside surface of the first section 502 (e.g., a surface configured to be in face-sharing contact with a support surface, such as a table, during conditions in which the first section 502 supports the head of the subject to be imaged). Similarly, the port 516 may be positioned at an underside surface of the second section 508, such that during operation of the abdominal RF coil assembly 500, the ports 518 and 516 are obscured from view. In this configuration, the ports may interface with one or more air pumps integrated with the support surface. For example, during imaging of the subject, the abdominal RF coil assembly 500 may be positioned on an MRI table. The MRI table may include one or more integrated air pumps configured to interface with the ports of the abdominal RF coil assembly 500 in order to pump air through the airflow passages 520 of the abdominal RF coil assembly 500. In some examples, air pumped through the abdominal RF coil assembly 500 may be directed back to the one or more air pumps for recirculation through the abdominal RF coil assembly 500. As another example, port 516 may act as an inlet port (e.g., port 516 may be coupled to an air pump) and port 518 may act as an outlet port, such that air first flows through the second and third sections before flowing to the first section.

As shown by FIG. 7, the abdominal RF coil assembly 500 includes RF coil array 702 having a plurality of RF coil elements 700. Each of the RF coil elements 700 may be a non-limiting example of the RF coil element 202 illustrated in FIG. 2 and described above, which includes a loop portion (e.g., comprised of at least two parallel, distributed capacitance wire conductors encapsulated and separated by a dielectric material) and a coupling electronics portion. The coupling electronics portion may include a pre-amplifier, a decoupling circuit, and an impedance inverter circuit, as described above. In the example shown by FIG. 7, the RF coil array 702 includes 98 RF coil elements in order to image the portion of the abdomen of the subject positioned against the second section 508 and third section 510 (e.g., with the third section 510 wrapped around the abdominal portion of the subject). However, in other configurations, the RF coil array 702 may include a different number of RF coil elements (e.g., 72 RF coil elements). Although the RF coil elements 700 are illustrated at the outer surfaces of the abdominal RF coil assembly 500, it should be appreciated that each RF coil may be embedded within a material of the second section 508 and third section 510 or otherwise secured (e.g., stitched) to an interior of the second section 508 and third section 510. FIG. 7 is included to illustrate a relative positioning of the RF coil elements within the interior of the abdominal RF coil assembly 500.

A coil-interfacing cable may extend between each coupling electronics portion of the RF coil elements 700 of the RF coil array 702 and an RF coil interfacing connector. Each of the electrical wires coupled to the corresponding coupling electronics portions may be housed together (e.g., bundled together) within the coil-interfacing cable and electrically coupled to the connector. The connector may interface with the MRI system (e.g., electrically couple with the MRI system by plugging into an input of the MRI system) in order to output signals from the RF coil elements to the MRI system, and the MRI system may process the signals received from the RF coil elements via the connector in order to produce images of the body of the patient (e.g., images of the anatomical features of the patient to be imaged by the abdominal RF coil assembly 500.

The internal electronics (e.g., coupling electronics portions, baluns, coil-interfacing cable) may be embedded within the material (e.g., embedded within the foam). In some examples, one or more of the sections may be covered in an outer cover to protect the internal components and maintain sterility, where the cover is thin and flexible (e.g., formed of a flexible material that is transparent to RF signals, such as one or more layers of Nomex® material or Nomex Nano® material).

In the configuration described above, during imaging of a subject (e.g., MR imaging via an MRI system coupled to the abdominal RF coil assembly 500, such as MRI apparatus 10 described above with reference to FIG. 1), the subject is positioned in contact with the abdominal RF coil assembly 500 such that the head of the subject is supported by the first section 502 and the abdominal portion of the subject is supported by the second section 508. The third section 510 is wrapped around the abdominal portion of the subject and flexibly conforms to the shape of the abdominal portion such that the RF coil elements 700 of the RF coil array 702 are positioned closely against the body of the subject at the abdominal portion for imaging of the abdominal portion via the MRI system. Additionally, the airflow passages 520 of the abdominal RF coil assembly 500 may receive air pumped via an air pump for cooling and/or heating of the abdominal RF coil assembly 500. For example, an air pump integrated into a table of the MRI system may interface with one or more ports of the abdominal RF coil assembly 500 in order to flow air through the airflow passages of the abdominal RF coil assembly 500. As a result, patient comfort may be increased.

Turning to FIG. 8, a flowchart is shown illustrating a method 800 for flowing air through one or more airflow passages of an RF coil assembly. In some examples, the RF coil assembly may be similar to the abdominal RF coil assembly 300 described above with reference to FIGS. 3-4, and/or the abdominal RF coil assembly 500 described above with reference to FIGS. 5-7. The one or more airflow passages may be similar to the airflow passages 332 shown by FIG. 4 and described above, and/or the airflow passages 527, 525, 529, and/or 520 described above with reference to FIG. 5. Instructions for carrying out method 800 and the rest of the methods included herein may be executed by a controller (e.g., electronic controller) based on instructions stored on a memory of the controller and in conjunction with signals received from sensors, such as sensors of an MRI system electronically coupled with the RF coil assembly. For example, the MRI system may include an air pump configured to pump air into the one or more airflow passages of the RF coil assembly, and may further include one or more temperature sensors configured to measure a temperature of the air being pumped into the one or more airflow passages and/or one or more airflow rate sensors configured to measure a flow rate of air pumped into the one or more airflow passages. The controller may employ actuators of the air pump and/or other components of the MRI system, for example, to adjust operation of the air pump and/or other components according to the methods described below.

At 802, RF coil assembly temperature and airflow rate are estimated and/or measured. In one example, the RF coil assembly may include a temperature sensor configured to measure a temperature of the RF coil assembly. The temperature of the RF coil assembly may be determined via an output of the temperature sensor of the RF coil assembly transmitted to an electronic controller of the MRI system (e.g., controller unit 25 of MRI apparatus 10 shown by FIG. 1 and described above). In another example, the temperature of the RF coil assembly may be estimated by an operator of the RF coil assembly (e.g., an MRI technician). The airflow rate includes a rate of air flowing through one or more airflow passages of the RF coil assembly. In one example, the airflow rate may be measured via a mass flow rate sensor positioned between an air pump of the MRI system and the one or more airflow passages of the RF coil assembly fluidly coupled with the air pump. In another example, the airflow rate may be measured based on an operating speed of the air pump. For example, higher air pump speeds may correspond to higher airflow rates, and lower air pump speeds may correspond to lower airflow rates. In yet another example, the airflow rate may be estimated by the operator of the RF coil assembly.

At 804, air is pumped through one or more airflow passages of the RF coil assembly. For example, the RF coil assembly may include one or more ports (e.g., port 326 shown by FIG. 4 and described above, port 518 shown by FIG. 5 and described above, etc.) fluidly coupled with one or more airflow passages disposed within an interior of one or more sections of the RF coil assembly. The one or more ports may be fluidly coupled with the air pump of the MRI system in order to pump air through the one or more airflow passages. The ports receiving the air pumped by the air pump may be referred to herein as input ports. In some examples, the MRI system may include a table or other support surface, and the air pump may be integrated with the table or other support surface such that positioning the RF coil assembly on the table or other support surface may fluidly couple the input ports of the RF coil assembly with the air pump. Additionally, the RF coil assembly may include one or more output ports adapted to flow air out of the airflow passages. In some examples, air may flow through the airflow passages and out of the output ports to return to the air pump, where the air pump may recirculate the air within the airflow passages.

At 806, the method includes determining whether cooling or heating of the RF coil assembly is desired. For example, the operator may determine at 806 that cooling the RF coil assembly would increase patient comfort (e.g., during conditions in which ambient air temperature is higher). As another example, the operator may determine at 806 that heating the RF coil assembly would increase patient comfort (e.g., during conditions in which ambient air temperature is lower). As a further example, cooling (or heating) demand may be determined based on a measured air temperature relative to a target air temperature and/or based on a current stage of an imaging protocol (e.g., once the RF coils have been active for a threshold amount of time, the method may determine that cooling is desired).

If cooling or heating of the RF coil assembly is not desired at 806, the method continues to 808 to maintain the temperature of the air pumped through the one or more airflow passages of the RF coil assembly. For example, the operator may maintain an operating speed of the air pump of the MRI system fluidly coupled with the airflow passages of the RF coil assembly. Further, the operator may maintain operating conditions of a heat exchanger of the MRI system positioned upstream of the airflow passages (e.g., fluidly coupled between the air pump and airflow passages) configured to adjust the temperature of the air pumped by the air pump. For example, at 808 the operator may maintain the heat exchanger in a condition in which the heat exchanger does not heat or cool the air pumped by the air pump (e.g., air pumped by the air pump may bypass the heat exchanger upstream of the airflow passages of the RF coil assembly).

If cooling or heating of the RF coil assembly is desired at 806, the method continues to 810 to increase or decrease the temperature of the air pumped through the one or more airflow passages of the RF coil assembly. For example, the MRI system may include one or more heat exchangers configured to heat or cool the air pumped by the air pump. As one example, the MRI system may include a heater (e.g., first heat exchanger) configured to heat the air pumped by the air pump upstream of the airflow passages during conditions in which heating of the air is selected by the operator (e.g., selected via a user interface of the MRI system, such as a user interface of display unit 33 shown by FIG. 1 and described above). The MRI system may additionally include a chiller (e.g., second heat exchanger) configured to cool the air pumped by the air pump upstream of the airflow passages during conditions in which cooling of the air is selected by the operator.

At 810, if heating of the air is desired, the operator may make a selection at the user interface of the MRI system to heat the air. In response, the controller of the MRI system may adjust a position of one or more valves fluidly coupling the air pump with the heater in order to increase a flow of air from the air pump to the heater to increase the temperature of the air. The air may then flow from the heater to the airflow passages of the RF coil assembly. If cooling of the air is desired, the operator may make a selection at the user interface of the MRI system to cool the air. In response, the controller of the MRI system may adjust the position of one or more valves fluidly coupling the air pump with the chiller in order to increase a flow of air from the air pump to the chiller to decrease the temperature of the air. The air may then flow from the chiller to the airflow passages of the RF coil assembly. In some examples, cooling the air may include closing one or more valves fluidly coupling the air pump to the heater, and heating the air may include closing one or more valves fluidly coupling the air pump to the chiller. Further, in some examples, the operator may set a desired temperature of the air flowing to the RF coil assembly, and the controller may adjust the position of one or more valves to adjust the airflow to the heater and/or chiller in order to achieve and maintain the desired temperature of air flowing to the RF coil assembly.

In yet another example, the MRI system may automatically regulate the temperature of the air flowing the one or more airflow passages of the RF coil assembly in response to a pre-determined target temperature of the RF coil assembly. For example, the pre-determined target temperature may be 70 degrees Fahrenheit. The controller (e.g., electronic controller) of the MRI system may continually monitor the temperature of the air flowing to the airflow passages of the RF coil assembly and may maintain the temperature at the pre-determined target temperature by adjusting the flow of the air from the air pump to one or each of the heater and chiller. The determination of whether cooling or heating of the RF coil assembly is desired at 806 may correspond to whether a difference between the temperature of the air flowing to the airflow passages of the RF coil assembly and the pre-determined target temperature is greater than a threshold difference (e.g., 3 degrees Fahrenheit). As one example, the pre-determined target temperature may be 70 degrees Fahrenheit, and the threshold difference may be 3 degrees Fahrenheit. During conditions in which the temperature of the air flowing to the airflow passages is greater than 73 degrees Fahrenheit, the controller may decrease the temperature of the air flowing to the airflow passages (e.g., increase the flow of air from the air pump to the chiller and/or decrease the flow of air from the air pump to the heater), and during conditions in which the air flowing to the airflow passages is less than 67 degrees Fahrenheit, the controller may increase the temperature of the air flowing to the airflow passages (e.g., increase the flow of air from the air pump to the heater and/or decrease the flow of air from the air pump to the chiller). In this configuration, the controller may continually adjust the temperature of the air flowing to the airflow passages of the RF coil assembly in order to regulate the temperature of the RF coil assembly, and patient comfort may be increased.

A technical effect of the abdominal RF coil assemblies described herein is increased depth of imaging of the abdominal region.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A radio frequency (RF) coil assembly for a magnetic resonance imaging (MRI) system, the RF coil assembly comprising:
    a support section configured to support a subject to be imaged;
    a first RF coil array disposed within the support section which comprises a first plurality of RF coil elements;
    a foldable section configured to wrap around an abdominal region of the subject;
    a second RF coil array disposed within the foldable section which comprises a second plurality of RF coil elements;
    wherein a plurality of airflow passages are disposed within the support and foldable sections;
    wherein the support section comprises:

a first section configured to support a head of the subject; and a second section configured to support an abdomen of the subject, wherein the first RF coil array is disposed within the second section; and wherein the second section includes a wedge base increasing in thickness from an inner edge of the second section to an outer edge of the second section;

further comprising an adjustable arm that couples the first section to the wedge base;

wherein the adjustable arm includes additional airflow passages fluidly coupling the airflow passages of the first section with the airflow passages of the second section.

2. The RF coil assembly of claim 1, wherein each RF coil element of the first and second RF coil arrays comprises a loop portion which includes two distributed capacitance wire conductors encapsulated and separated by a dielectric material.

3. The RF coil assembly of claim 1, wherein the support and foldable sections are made of different materials, and wherein a material of the foldable section is more flexible than a material of the support section.

4. The RF coil assembly of claim 1, further comprising the adjustable arm coupling the first section to the second section, wherein the adjustable arm is configured to adjust a distance between the first section and the second section.

5. The RF coil assembly of claim 4, wherein the adjustable arm is configured to rotate the first section relative to the second section in accordance with different body positions of the subject.

6. The RF coil assembly of claim 1, wherein a plurality of orifices are formed on a surface of the support section and adapted to be in face-sharing contact with the subject, the plurality of orifices being fluidly coupled to corresponding airflow passages.

7. The RF coil assembly of claim 1, wherein the wedge base is configured to be positioned against the abdomen of the subject during operation.

8. The RF coil assembly of claim 1, wherein the plurality of airflow passages coupled to a temperature sensor and a controller is configured to utilize output from the temperature sensor to automatically maintain the temperature of the air flowing in the plurality of airflow passages at or below a threshold temperature.

9. The RF coil assembly of claim 1, wherein the first section includes a first extension, a second extension, and an opening formed between the first extension and second extension.

10. The RF coil assembly of claim 9, wherein the first extension and the second extension curve around the opening such that the first section forms a U-shape having a first side and an opposing second side.

11. The RF coil assembly of claim 9, wherein the inner edge is a first edge positioned toward the first extension of the first section and the outer edge is a second edge positioned opposite to the inner edge, away from the first extension of the first section.

12. The RF coil assembly of claim 1, wherein the wedge base is joined with an extension portion coupled to the first section, with the extension portion having a reduced size relative to the wedge base.

13. The RF coil assembly of claim 1, wherein the thickness of the wedge base increases as the wedge base extends toward the adjustable arm.

* * * * *